(12) United States Patent
Bonrath et al.

(10) Patent No.: US 8,802,898 B2
(45) Date of Patent: Aug. 12, 2014

(54) ISOMERIZATION OF β-KETO-ALLENES

(75) Inventors: Werner Bonrath, Basel (CH); Reinhard Karge, Basel (CH); Thomas Netscher, Basel (CH); Yann Pressel, Rixheim (FR)

(73) Assignee: DSM IP Assets B.V., Heerlen (NL)

( * ) Notice: Subject to any disclaimer, the term of this patent is extended or adjusted under 35 U.S.C. 154(b) by 102 days.

(21) Appl. No.: 13/642,047

(22) PCT Filed: Apr. 18, 2011

(86) PCT No.: PCT/EP2011/056106
§ 371 (c)(1),
(2), (4) Date: Apr. 5, 2013

(87) PCT Pub. No.: WO2011/131607
PCT Pub. Date: Oct. 27, 2011

(65) Prior Publication Data
US 2013/0197272 A1 Aug. 1, 2013

(30) Foreign Application Priority Data
Apr. 19, 2010 (EP) .................... 10160356

(51) Int. Cl.
C07C 45/67 (2006.01)
(52) U.S. Cl.
USPC ........................................ 568/384
(58) Field of Classification Search
CPC .............................. B01J 31/08; B01J 2231/52
USPC ........................................ 568/384
See application file for complete search history.

(56) References Cited

FOREIGN PATENT DOCUMENTS

EP 0 647 624 4/1995
WO WO 2008/092655 8/2008

OTHER PUBLICATIONS

International Search Report for PCT/EP2011/056106 mailed Oct. 5, 2011.
S. Julia et al., "Memoires Presentes a la societe chimique. Nr. 517.—Transposition homoallyluique vinylogue d alcools Aplha, Beta, Gamme, Delta-dieniques Epsilon-cyclopropaniques", Bulletin De La Societe Chimique De France, Societe Francaise De Chimie, Paris, Jan. 1, 1964, pp. 3218-3226.

*Primary Examiner* — Sikarl Witherspoon
(74) *Attorney, Agent, or Firm* — Nixon & Vanderhye P.C.

(57) ABSTRACT

Isomerization of β-keto-allenes of the general formula I wherein $R^1$ is hydrogen, methyl or ethyl, in particular hydrogen or methyl; $R^2$ is hydrogen or methyl; $R^3$ is hydrogen or methyl, in particular methyl and $R^4$ is an aliphatic hydrocarbon residue containing 1-37 carbon atoms, into corresponding α,γ-dienones of formula II by treatment with a basic ion exchange resin.

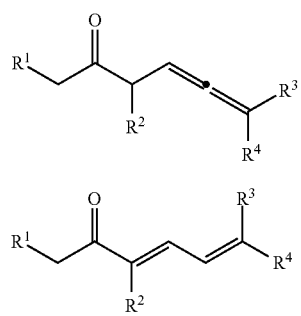

10 Claims, 1 Drawing Sheet

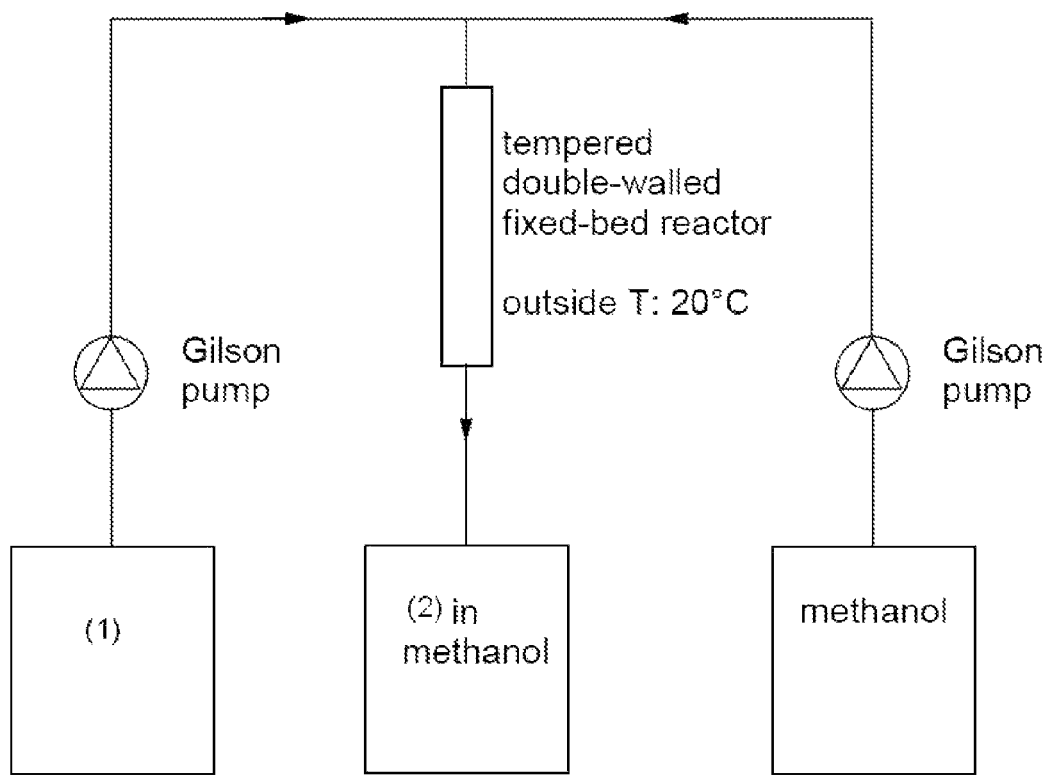

ISOMERIZATION OF β-KETO-ALLENES

This application is the U.S. national phase of International Application No. PCT/EP2011/056106 filed 18 Apr. 2011 which designated the U.S. and claims priority to EP 10160356.1 filed 19 Apr. 2010, the entire contents of each of which are hereby incorporated by reference.

The present invention relates to the isomerization of β-keto-allenes. More specifically, the present invention relates to the isomerization of β-keto-allenes to α,γ-dienones under catalysis of basic ion exchange resins.

α,γ-Dienones are interesting compounds for the flavour and fragrance industry and valuable intermediates in the synthesis of carotenoids and vitamins A (Carotenoids, ed. O. Isler, Birkhäuser Verlag Basel and Stuttgart, 1971). The preparation of α,γ-dienones from β-keto-allenes is known in the art.

Saucy et al. (Helv. Chimica Acta 50, 1158-1167 [1967]) have described the preparation of β-keto-allenes and their isomerization into conjugated dienones (α,γ-dienones) in an exothermic reaction in the presence of alcoholic alkali in petroleum ether (two-phase system) at 10° C. Thus, e.g., 6-methyl-3,5-heptadien-2-one, pseudoione and pseudoiron were obtained.

WO 2008/092655 A1 discloses the isomerization of β-keto-allenes to α,γ-dienones with aqueous sodium hydroxide in methanol under temperature control with dry-ice/alcohol bath because of the strongly exothermic reaction.

EP 0 418 690 discloses the isomerization of 8-(2'2'-dimethylcyclopropyl)-6-methyl-4,5-octadien-2-one in an organic solvent with a strong organic or mineral acid or with a strong aqueous base (30%-50% NaOH or KOH) in an alcohol (methanol or ethanol) at 0° C.-10° C. (see, e.g., Saucy et al., supra). The use of acidic ion exchange resins, e.g., Amberlite IR 120, etc., has also been mentioned, however, without exemplification.

EP 0 647 624 describes the isomerization of the $C_{18}$-β-keto-allene 8-(1,1,5-trimethly-cyclo-4-hexenyliden)-6-methyl-octa-4,5-dien-2-one into 8-(1,1,5-trimethyl-cyclo-5-hexenyl)-6-methyl-3,5,7-trien-2-one (a $C_{18}$-intermediate in the synthesis of vitamin A) by treatment with hydrobromic acid in acetone under cooling to about 0° C. By treatment of the $C_{18}$-β-keto-allene in methylene chloride with diazabicycloundecene or in methanol with sodium carbonate 8-(1,1,5-trimethyl-cyclo-4-hexenyliden)-6-methyl-3,5-octadien-2-one is obtained.

According to Ullmann's Encyclopedia of Industrial Chemistry, 5th, completely revised edition, Vol. A5, 1986, p. 344, the catalytic activity of organic ion exchangers can be used advantageously in many important industrial reactions. Isomerization reactions are not among those which have been mentioned specifically let alone the isomerization of β-keto-allenes into α,γ-dienones.

Starting from the task of developing commercially attractive methods of isomerization of β-keto-allenes into α,γ-dienones which can be conducted preferably continuously and avoid the use of acidic or basic solvents which have to be neutralized during work-ups it has been found that basic ion exchange resins can be used advantageously as catalysts in this isomerization.

The present invention, therefore, relates to the isomerization of β-keto-allenes of the general formula

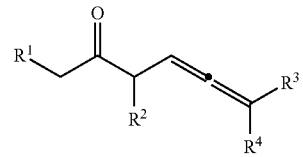

wherein
$R^1$ is hydrogen, methyl or ethyl, in particular hydrogen or methyl;
$R^2$ is hydrogen or methyl;
$R^3$ is hydrogen or methyl, in particular methyl and
$R^4$ is an aliphatic hydrocarbon residue containing 1-37 carbon atoms, into corresponding α,γ-dienones of formula

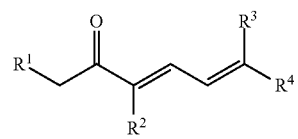

by treatment with a basic ion exchange resin, preferably a strongly basic, macroporous ion exchange resin.

Aliphatic hydrocarbon residues containing 1-37 carbon atoms in formulae I and II comprise those which represent residues in compounds of interest in the flavour or fragrance industry or which are intermediates in the manufacture of carotenoids and vitamins A in their broadest sense. Under this aspect such residues encompass straight and branched chain residues, saturated or ethylenically and/or ethinically unsaturated, which again may be substituted with lower alkyl groups, particularly methyl or ethyl groups, or with $C_{3-6}$-cyloalkyl and -cycloalkenyl groups, or which may contain such cyclic residues within the carbon chain. In preferred embodiments residue $R^4$ is a 2-(2'2'-dimethylcyclopropyl)-ethyl group, a group represented by formula (A)=—[(CH$_2$)$_3$—CH(R$^5$)]$_x$—CH$_3$ or formula (B)=—[CH$_2$—CH$_2$—CH=C(R$^5$)]$_y$—CH$_3$, wherein x and y are 1-6, preferably 1-4, and $R^5$ is hydrogen, methyl or ethyl. Preferred examples of such groups are —(CH$_2$)$_3$—CH(CH$_3$)—(CH$_2$)$_3$—CH(CH$_3$)$_2$ and —CH$_2$—CH$_2$—CH=C(CH$_3$)$_2$.

The expressions "basic anion exchange resin" and "strongly basic anion exchange resin" are well known to persons skilled in the art of ion exchange, and many useful review articles concern ion exchangers, inter alia strongly basic anion exchange resins such as in Ullmann's Encyclopedia of Industrial Chemistry, Vol. A 14 (1989), "Ion Exchangers", pages 394-459, of which pages 397-400 are particularly pertinent regarding different types of resins, cross-linking, porosity and exchange capacity. In general, ion exchange resins featuring quaternary ammonium groups are strongly basic, and both "type I (or 1)" and "type II (or 2)" resins are suitable for use in the process of the present invention, provided they are also "macroporous". The latter term as used herein denotes any resin which has a higher degree of cross-linking than a gel resin (such as AMBERLITE® IRA 400). The pore diameter in a typical macroporous resin is about 100 nm as compared to about 1 nm in a gel resin (see, besides Ullmann's Encyclopedia, supra, DIN 54 400, "Ionenaustausch-Begriffe", 1987, p. 7). Apart from the many sources of information in the scientific literature, the catalogues of suppliers of ion exchangers categorize their products appropriately such that selecting a "strongly basic, macroporous anion exchange resin" for use in the process of the present invention is no problem for a person skilled in the art.

For the purpose of the present invention, the preferred strongly basic macroporous anion exchange resins are those featuring a polystyrene matrix with quaternary ammonium cations and hydroxyl anions supplied by several producers, e.g., by Röhm & Haas Deutschland GmbH, Frankfurt/Main, Germany; Purolite Company, Bala Cynwyd, Pa., USA (representative: Staerkle & Nagler AG, Zurich, Switzerland); Dow Chemical Co., Midland, Mich., USA and Bayer AG, Leverkusen, Germany. Suitable strongly basic macroporous anion exchange resins are known under the trademarks DUOLITE®, AMBERLITE®, PUROLITE®, DOWEX®, LEWATIT®, etc. Strongly basic macroporous anion exchange resins featuring a polyacrylic matrix rather than a polystyrene matrix can also be used in the process of the present invention but are less preferred than those with a polystyrene matrix.

Especially preferred in the isomerization of the present invention are basic anion exchange resins Amberlite® IRA 900, Dowex® MSA-1, Diaion® HPA25 or PA308 as well as Amberlysts® A260H, XE-4, XE-8, XE-8 new and XE-10 from Röhm & Haas and equivalent resins with same chemical structure and similar physico-chemical properties.

The amounts of resins to be used as catalysts can vary within wide ranges and depend on their physico-chemical structure. Optimal amounts can easily be determined empirically.

The isomerization is conveniently carried out in a $C_{1-6}$-alcohol, preferably a $C_{1-3}$-alcohol. with methanol being preferred, at a temperature in the range of −10° C. to 30° C., preferably in the range of 0° C. to 10° C. The reactor is conveniently a fixed bed reactor. Since the isomerization is exothermic the reaction is effected under cooling according to methods well-known in the art. In order to reduce undesirable heating (hot spots at the catalyst) it may be advantageous to dilute the catalyst by adding/mixing it with a neutral polymerisate, e.g., a macroporous polystyrene cross-linked with divinylbenzene without functional groups, such as MN270, obtainable from Purolite Company.

EXPERIMENTAL PART

General

All reactions were carried out under argon.

Flash chromatography (excess argon pressure ≤0.2 bar) was performed on Merck silica gel 60 (0.040-0.063 mm) and thin layer chromatography was performed on silica gel F254 plates; detection by UV (254 nm) and by spraying with a vanillin revelator (prepared from the sequential addition of 22 g vanillin, 830 g ethanol, 100 g ice and 100 mL of concentrated sulfuric acid) followed by heating with a heat gun.

Resins:

The wet A26OH, with R-NMe3OH groups, was purchased from Rohm and Haas (Lot. 0003260540); concentration of active sites >1.19 mmol/g; moisture holding capacity: 66-75%. A26OH has a strong base capacity of 1.002 (mol/L), a total base capacity of 1.019 (mol/L), a total weight capacity of 4.007 (mmol/g) for the dry ion exchange resin and a moisture holding capacity of 68.01%. XE-8-new has a strong base capacity of 0.681 (mol/L), a total base capacity of 0.783 (mol/L), a total weight capacity of 3.974 (mmol/g) for the dry ion exchange resin and a moisture holding capacity of 70.31%. The catalysts were used as received. MN270, which is a macroporous polystyrene crosslinked with divinylbenzene, was purchased from Purolite and used as received.

Analyses:

NMR spectroscopy: at 298 K on Bruker Avance-300 spectrometer with $CDCl_3$ as solvent (Armar chemicals, stabilized with silver and containing 0.03 V/V % tetramethylsilane) at 300 MHz for $^1$H-NMR and 75 MHz for $^{13}$C-NMR; chemical shifts δ in ppm relative to tetramethylsilane, coupling constants J in Hz. Quantitative $^1$H-NMR were measured on Bruker Avance-300 spectrometer with 1,4-dimethoxybenzene (DMB; Fluka) as internal standard for the analyses of (1), (2) and (3).

Quantitative GC analysis of (4) was carried out with a gas chromatograph HP 6890 [capillary column Agilent DB-1701 (fused silica); 30 m×0.32 μm, film 0.1 μm, 1.5 mL/min He, T=70° C. for 1 min, 10° C./min, 280° C. for 7 min)] equipped with an autosampler HP 7683, split injector and FID; tR in min.

GC analysis of (6) was performed with a gas chromatograph HP 6890 [capillary column Optima-1 (fused silica), 30 m×0.53 μm, film 3.0 μm, 3.6 mL/min He, T=50° C. for 10 min, 6.0° C./min for 11.67 min, 10° C./min for 18 min] equipped with an autosampler HP 7683, split injector and FID; tR in min.

GC-MS analysis was performed with a HP 6890 [capillary column Restek Rtx5 SilMS with 5% phenyl methyl silicone (fused silica), 30 m×0.28 mm, film 0.5 μm, 1.50 mL/min He, T=70° C., 10.0° C./min for 15 min] and El at 70 eV.

Apparatus (FIG. 1):

Pumps of Gilson type 305, a Huber thermostat type "ministat", and a double-walled fixed-bed glass reactor (with a frit (porosity 0), length 18.5 cm, 6 mm inner diameter) were used.

The following Examples illustrate the present invention in more detail.

EXAMPLE 1

(a) Isomerization of 6,10,14-trimethyl-pentadeca-4,5-dien-2-one (1) In Batch Mode To 6,10,14-trimethyl-pentadeca-3,5-dien-2-one (2)

In a 25 mL two-neck-flask equipped with a septum and an argon bubbler, the basic ion exchange resin A26OH (0.25 g, ≥0.3 mmol) was stirred in methanol (ca. 3 mL) for 15 minutes. The solvent was removed by pumping it out with a micro-filtercandle. Methanol (2.5 mL) was added to the catalyst and cooled down to an inner temperature of 1-3° C. (ice bath). The β-keto allene (1) (5.00 g with a purity 70.4 wt %, 13.31 mmol) was then added drop-wise within 5 minutes by syringe to the stirred catalyst. The temperature reached 6° C. After the addition the reaction mixture was stirred below 25° C. After 120 min of reaction the solution was separated from the catalyst by pumping it out with a micro-filter candle. The catalyst was washed two times with 3 mL methanol and could then be used for the next run. The methanol solution containing the crude product was concentrated in vacuo (40 mbar, 40° C.). The isolated yellow oil was analyzed by quantitative 1H-NMR (formed (3E)-(2), (3Z)-(2) and remaining (1) with DMB as internal standard. The results are indicated in Table 1.

TABLE 1

| run | (3E)/(3Z)-(2) ratio | total yield [%] | remaining (1) [%] | conversion [%] | selectivity [%] |
|---|---|---|---|---|---|
| 1 | 85/15 | 87.99 | 0.55 | 99.45 | 88.48 |
| 2 | 100/0 | 89.30 | 0.99 | 99.01 | 90.19 |
| 3 | 101/−1 | 89.52 | 1.79 | 98.21 | 91.15 |
| 4 | 100/0 | 91.73 | 1.87 | 98.13 | 93.48 |
| 5 | 99/1 | 90.54 | 1.32 | 98.68 | 91.75 |
| 6 | 99/1 | 90.37 | 2.25 | 97.75 | 92.45 |
| 7 | 100/0 | 88.53 | 2.81 | 97.19 | 91.09 |
| 8 | 99/1 | 91.72 | 2.84 | 97.16 | 94.40 |
| 9 | 99/1 | 92.58 | 4.73 | 95.27 | 97.18 |
| 10 | 99/1 | 89.17 | 6.14 | 93.86 | 95.00 |

(b) Isomerization of (1) To (2) In Continuous Reaction Mode

A vertical double-walled fixed-bed glass reactor (with a frit, porosity 0, length 18.5 cm, 6 mm inner diameter) was cooled at 20° C. with a thermostat. The upper part of the reactor was connected through a T-junction to two Gilson pumps by Teflon tubes. The lower part of the reactor was connected to a bottle with a Teflon tube. The catalyst A26OH (0.50 g, ≥0.60 mmol) and MN270 (1.00 g; a macroporous polystyrene crosslinked with divinylbenzene, used to dilute the catalyst) were stirred in ca. 10 mL of methanol for 15 minutes and then transferred into the reactor. The level of the solution in the reactor was kept over the catalyst bed (h=4.5 cm, V=5.1 mL), controlled by siphon effect. The β-keto allene (1) (purity 85.3%) and methanol were separately pumped with a flow rate of 0.09 and 0.04 mL/min, respectively, into the two horizontal inlets of the T-junction fixed on the top of the continuous reactor. The so formed solution of 14 (17.10 mmol/mL) in methanol flew from the T-junction outlet into the reactor. Samples were taken regularly, concentrated in vacuo (40 mbar, 40° C.) and analyzed by quantitative $^1$H-NMR. The feeding was stopped after 24 hours. The solvent of the collected solution was evaporated in vacuo (40 mbar, 40° C.) and the isolated yellow oil analyzed by quantitative $^1$H-NMR (formed (3E)-(2), (3Z)-(2) and remaining (1) with 1,4-dimethoxybenzene (DMB) as internal standard). The results are indicated in Table 2.

TABLE 2

| time [min] | (3E)/(3Z)-(2) ratio | total yield [%] | remaining (1) [%] | conversion [%] | selectivity [%] |
|---|---|---|---|---|---|
| 195 | 99/1 | 94.50 | 5.42 | 94.58 | 99.90 |
| 435 | 100/0 | 90.78 | 7.70 | 92.30 | 98.35 |
| 615 | 99/1 | 90.09 | 8.54 | 91.46 | 98.51 |
| 795 | 99/1 | 88.00 | 11.91 | 88.09 | 99.90 |
| 1035 | 98/2 | 86.02 | 13.88 | 86.12 | 99.89 |
| 1215 | 97/3 | 82.22 | 17.70 | 82.30 | 99.90 |
| 1440 | 97/3 | 78.07 | 21.33 | 78.67 | 99.24 |
| total | 99/1 | 89.50 | 10.97 | 89.03 | 99.41 |

The apparatus is shown in FIG. 1.

EXAMPLE 2

Isomerization of 6,10-dimethyl-undeca-4,5,9-trien-2-one (3) To 6,10-dimethyl-undeca-3,5,9-trien-2-one (4) In Repeated Batch Mode In a 25 mL two-neck-flask equipped with a septum and an argon bubbler, the basic ion exchange resin A26OH (0.25 g, ≥0.3 mmol) was stirred in methanol (ca. 3 mL) for 15 minutes. The solvent was removed by pumping it out with a microfiltercandle. Methanol (2.5 mL) was added to the catalyst and cooled down to an inner temperature of 1-3° C. (ice bath). The β-keto allene (3) (7.08 g with a purity of 91%, 33.2 mmol) was added drop-wise within 10 minutes by syringe to the stirred catalyst. The temperature reached 6° C. After the addition the reaction mixture was stirred between 1-3° C. After 180 minutes of reaction the solution was separated from the catalyst by pumping it out with a micro-filter candle. The catalyst was washed two times with 3 mL of methanol and could then be used for the next run. The mixture containing the crude product was concentrated in vacuo (40 mbar, 40° C.). The isolated yellow oil was analyzed by quantitative GC (for (5Z)-(4):(5E)-(4) ratio and yield determination). The results are indicated in Table 3.

TABLE 3

| run | (5Z)/(5E)-4 ratio | total yield [%] | remaining (3) [%] | conversion [%] | selectivity [%] |
|---|---|---|---|---|---|
| 1 | 61/39 | 94.27 | 0.00 | 100.00 | 94.27 |
| 2 | 61/39 | 95.72 | 0.00 | 100.00 | 95.72 |
| 3 | 61/39 | 94.75 | 0.93 | 99.07 | 95.64 |
| 4 | 61/39 | 92.24 | 1.42 | 98.58 | 93.57 |
| 5 | 61/39 | 92.19 | 3.00 | 97.00 | 95.04 |
| 6 | 61/39 | 87.08 | 6.57 | 93.43 | 93.20 |
| reactivation | | | | | |
| 7 | 62/38 | 81.48 | 0.00 | 100.00 | 81.48 |
| 8 | 61/39 | 83.90 | 3.81 | 96.19 | 87.22 |
| 9 | 61/39 | 77.24 | 10.07 | 89.93 | 85.88 |

Reactivation of the catalyst was carried out when the yield was lower than 50%. The catalyst was reactivated by addition of 2 mL of aqueous 1 M sodium hydroxide, stirring for 30 minutes, removal of the solution by pumping it into a gas washing flask with a micro-filter candle. The ion exchange resin was then stirred in 2 mL of distilled water for 5 minutes and the solution was removed. This was repeated four more times. The pH was neutral for the third and fourth repeat. The catalyst was finally stirred in 2 mL of methanol for 15 minutes.

With basic exchange resin XE-8-new, the same procedure was used for the repeated batch isomerization with 7.08 g of (3) (purity 86%, 31.3 mmol). Results are given in Table 4.

TABLE 4

| run | (5Z)/(5E)-4 ratio | total yield [%] | remaining (3) [%] | conversion [%] | selectivity [%] |
|---|---|---|---|---|---|
| 1 | 62/38 | 96.67 | 0.00 | 100.00 | 96.67 |
| 2 | 62/38 | 96.92 | 4.00 | 98.57 | 98.33 |
| 3 | 62/38 | 93.44 | 6.00 | 94.00 | 99.40 |

First reactivation: addition of 2 mL of aqueous 1 M sodium hydroxide, stirring for 35 minutes, removal of the solution by pumping it into a gas washing flask with a micro-filter candle. The ion exchange resin was then stirred in 2 mL of distilled water for 5 minutes and the solution was removed. This was repeated four more repeat. The pH was neutral for the fourth and fifth times. The catalyst was finally stirred in 2 mL of methanol for 15 minutes at least. Second reactivation: addition of 2 mL of aqueous 1 M sodium hydroxide, stirring for 17 hours, removal of the solution by pumping it into a gas washing flask with a micro-filter candle. The ion exchange resin was then stirred in 2 mL of distilled water for 1 hour and the solution was removed; this was repeated two more times. The pH was neutral for the second repeat. The catalyst was finally stirred two times in 2 mL of methanol for 1 hour. Then methanol was added for the next run.

EXAMPLE 3

Isomerization of 6-methyl-hepta-4,5-dien-2-one (5) Tto 6-methyl-hepta-3,5-dien-2-one (6) In Batch Mode In a 25 mL two-neck-flask equipped with a septum and an argon bubbler, the basic ion exchange resin A26OH (0.25 g, ≥0.3 mmol) was stirred in methanol (ca. 3 mL) for 15 minutes. The solvent was removed by pumping it out with a microfilter candle. Methanol (2.5 mL) was added to the catalyst and cooled down to an inner temperature of 1-3° C. (ice bath). The β-keto allene (5) (4.62 g with a 90% area GC, 33.5 mmol) was then added drop-wise by syringe to the stirred catalyst. The inner temperature was maintained between 1-9° C. After 75 minutes no 5 could be detected by GC. The solution was separated from the catalyst by pumping it out with a microfilter candle. The catalyst was washed two times with 3 mL of methanol. The mixture containing the crude product was concentrated in vacuo (40 mbar, 40° C.) affording a yellow oil (4.72 g). Purification of 1.54 g by flash chromatography (hexane/ethyl acetate 97:3, $R_f$=0.11) allowed to recover 1.16 g (75%) of purified (6). Coconut smell.

GC: (Z)-6 $t_R$=25.00 and (E)-6 $t_R$=26.26. (E/Z) 95:5

$^1$H-NMR of (E)-6: 1.90 (s, 3H, CH$_3$—C—CH$_3$), 1.92 (s, 3H, CH$_3$—C—CH$_3$), 2.27 (s, 3H, CH$_3$C=O), 6.00 (d, J=12 Hz, 1H, (CH$_3$)$_2$C=CH), 6.01 (d, J=15 Hz, 1H, O=C—CH=), 7.42 (dd, J=12 Hz, J=15 Hz, 1H, =CH—CH=CH).

$^{13}$C-NMR (E)-6: 19.0 (CH$_3$—C), 26.6 (CH$_3$—C), 27.4 (CH$_3$—CO), 124.1 ((CH$_3$)$_2$C=CH), 128.0 (O=C—CH=), 139.5 (=CH—CH=CH), 147.5 (C—(CH$_3$)$_2$), 198.7 (CO).

An analytic sample was prepared according to the procedure of Saucy and Marbet (Helv. Chim. Acta 1967, 50, 1158-67 [1]).

GC: (Z)-(6) $t_R$=25.00 and (E)-(6) $t_R$=26.26. (E/Z) 87:13 (Lit.: 86:14 [1])

GC-MS: (Z)-(6) $t_R$=5.44, m/z 43, 81, 109 [M$^+$—CH$_3$], 124 [M$^+$].

(E)-(6) $t_R$=6.22, m/z 43, 81, 109 [M$^+$—CH$_3$], 124 [M$^+$].

EXAMPLE 4

Comparison of A260H Resin in Batch Experiments with NaOH According to Method of Saucy and Marbet [1967]

The comparison of A260H in batch experiments with NaOH shows two main trends: The turnover numbers (TON) were higher with A260H for (3) to (4), viz. 620 (for 6 runs) versus 94 (used only once). The turnover frequencies (TOF) were lower with A260H for (3) to (4), viz. 34 h$^{-1}$ (for 6 runs) versus 188 h$^{-1}$. Independent from the catalyst used in the isomerization the reaction is faster with smaller alkyl chains in the keto allene.

The invention claimed is:

1. Isomerization of β-keto-allenes of the general formula

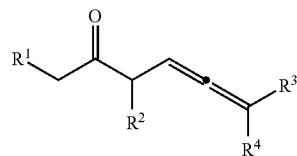

wherein
R$^1$ is hydrogen, methyl or ethyl;
R$^2$ is hydrogen or methyl;
R$^3$ is hydrogen or methyl, and
R$^4$ is an aliphatic hydrocarbon residue containing 1-37 carbon atoms,
into corresponding α,γ-dienones of formula

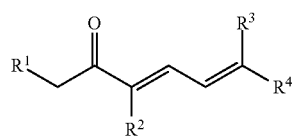

by treatment with a basic ion exchange resin.

2. The isomerization of claim 1 wherein the basic ion exchange resin is a strongly basic, macroporous resin.

3. The isomerization of claim 1, wherein in formula I R$^4$ is 2-(2'2'-dimethylcyclopropyl)-ethyl.

4. The isomerization of claim 1, wherein in formula I R$^4$ is a residue A=—[(CH$_2$)$_3$—CH(R$_5$)]$_x$—CH$_3$ with R$^5$=hydrogen, methyl or ethyl and x=whole number from 1 to 6.

5. The isomerization of claim 1, wherein in formula I R$^4$ is a residue B=—[CH$_2$—CH$_2$—CH=C(R$^5$)]$_y$—CH$_3$ with R$^5$=hydrogen, methyl or ethyl and y=whole number from 1 to 6.

6. The isomerization of claim 1, wherein the compound of formula I is 6,10,14-trimethyl-pentadeca-4,5-dien-2-one.

7. The isomerization of claim 1, wherein the compound of formula I is 6,10-dimethyl-undeca-4,5,9-trien-2-one.

8. The isomerization of claim 1, wherein the compound of formula I is 6-methyl-hepta-4,5-dien-2-one.

9. The isomerization of claim 1 wherein the basic anion exchange resin is of type 1 or of type 2.

10. The isomerization of claim 1 which is run in continuous mode with regeneration of the anion exchange catalyst.

* * * * *